United States Patent
Matkovich

Patent Number: 5,126,054
Date of Patent: Jun. 30, 1992

[54] VENTING MEANS

[75] Inventor: Vlado Matkovich, Glen Cove, N.Y.

[73] Assignee: Pall Corporation, Glen Cove, N.Y.

[21] Appl. No.: 528,160

[22] Filed: May 24, 1990

[51] Int. Cl.$^5$ ............................................. B01D 39/00
[52] U.S. Cl. .................................. 210/641; 210/436; 210/472
[58] Field of Search ............... 210/641, 436, 445, 446, 210/472; 55/159; 604/123, 122, 126

[56] References Cited

U.S. PATENT DOCUMENTS

| | | | |
|---|---|---|---|
| 2,781,064 | 2/1957 | Dawkins | 141/54 |
| 3,149,758 | 9/1964 | Bush | 222/189 |
| 3,364,658 | 1/1968 | Walker | 55/171 |
| 3,394,533 | 7/1968 | Li | 55/337 |
| 3,523,408 | 8/1970 | Rosenberg | 55/159 |
| 3,631,654 | 1/1972 | Eddy | 55/159 |
| 3,650,093 | 3/1972 | Rosenberg | 604/123 X |
| 3,803,810 | 4/1974 | Rosenberg | 55/159 |
| 4,223,695 | 9/1980 | Muetterties | 55/159 X |
| 4,294,594 | 10/1981 | Sloane et al. | 55/186 |
| 4,360,435 | 11/1982 | Bellamy et al. | 210/636 |
| 4,900,308 | 2/1990 | Verkaart | 604/126 |
| 4,915,847 | 4/1990 | Dillon et al. | 210/737 |

OTHER PUBLICATIONS

Brochure, "Pall Ultipor I.V. Filter/Air Eliminator", Aug. 1980.

*Primary Examiner*—Frank Spear
*Attorney, Agent, or Firm*—Leydig, Voit & Mayer

[57] ABSTRACT

Venting means for venting gas from the transfer line of a liquid delivery system comprising a housing, a first, liquid-wettable, microporous membrane carried in said housing so as to be in communication with the transfer line, a second, non-liquid-wettable, gas permeable microporous membrane superimposed on said microporous membrane to the outward side of the housing. Gas in the delivery system is vented from the system so long as the first microporous membrane remains unwetted by the delivery liquid.

19 Claims, 2 Drawing Sheets

VENTING MEANS

FIELD OF THE INVENTION

The present invention relates generally to a liquid-gas separator, and more particularly to a venting means and method for the removal of gases from a liquid delivery or transfer system.

Frequently, it is necessary to transfer a liquid from one holding container to another or to deliver a liquid from a storage container without entraining in the liquid to be transferred gas that may be present in the delivery or transfer system, such as the transfer line. Venting of such gases can be particularly important in the in-line filtration of blood and blood components from a donor bag to a receiving bag, such as, for example, in the filtering of blood and blood components to remove leukocytes or the like.

Further, in many medicinal injections, such as percutaneous injections, including intravenous feeding and the like, it is generally customary to clear the line of air before injecting the liquid, but the problem of air entering the line after priming the administration set and being injected with the liquid cannot be entirely foreclosed. This is, of course, undesirable for air cannot be injected concurrently with the injection of liquid into the patient without the danger of an embolism, with possibly fatal consequences.

Accordingly, it would be highly desirable to be able to vent gas that may be present in such devices with the assurance that gas would be completely removed from the system, and could not reenter the system.

SUMMARY OF THE INVENTION

In accordance with one aspect of the instant invention, a gas vent means is provided that is capable of venting gases in a liquid transfer or delivery system. The vent means includes a housing, a first microporous membrane that is wettable by the liquid to be transferred or delivered by the system and a second microporous membrane, capable of passing gas therethrough but which is not wettable by the liquid to be transferred. The first, liquid-wettable, microporous membrane and the second, non-wettable, microporous membrane are so positioned in the housing of the vent means that the first, liquid-wettable, microporous membrane becomes saturated with liquid during the liquid transfer operation before the non-wettable layer is contacted by the liquid. Before the first, liquid-wettable, microporous membrane is saturated with liquid, it is capable of passing gas therethrough so that gas in the system is vented by passing through both membrane layers. After the first, liquid-wettable, microporous membrane becomes saturated with liquid, a condition which occurs after gas in the transfer line has been purged from the delivery system, the first microporous membrane is no longer capable of passing gas therethrough so the first microporous membrane forecloses the ingress of gases from outside the transfer system into the transfer system.

The venting means of the present invention is particularly well adapted for use in pharmaceutical and medicinal applications and in medical devices where gases present in such systems must be vented or where gases must be prevented from reaching a patient receiving an injection of the liquid. The apparatus and method of the present invention may be used quite satisfactorily where it is desirable to maintain a sterile environment in the liquid transfer or delivery system, after gas present therein is removed, and it is suitable for use in closed systems to preserve the sterility thereof. More broadly, it will be appreciated that the vent means of the present invention is useful in any liquid transfer or delivery system where there is to be a one time removal of gases from the system and the ingress of gases into the system during liquid transfer or delivery is to be prevented, including, for example, such systems that are to be primed for future liquid transfer or systems that are to be filled to a predetermined level.

In accordance with another aspect of the present invention, there is provided a closed liquid transfer system for the filtration of blood and blood components which includes venting means as described above. In this embodiment, as a column of blood or blood components is passed from a storage reservoir containing the liquid to be filtered, through a filter means for filtering undesirable matter from the blood or blood components and into a receiving reservoir, the column of liquid displaces gas present in the transfer line leading from the storage reservoir to the receiving reservoir, as well as gas in the filter means, and drives the gas through venting means disposed in the transfer line downstream of the filter and upstream of the receiving reservoir. After gas is passed through the venting means, liquid in the transfer line contacts the first, liquid-wettable, microporous membrane of the venting means to effectively seal the vent, and thus the transfer system, from the ingress of gases outside the closed system. In this way, a sterile environment is maintained in the closed system.

In accordance with yet another aspect of the present invention, a method for priming a liquid delivery system is provided. Liquid from a storage reservoir is caused to pass into a liquid transfer line, and, as the liquid moves through the transfer line, gas in a line is driven ahead of the moving column of liquid until the gas contacts the venting means where it is vented.

DESCRIPTION OF THE PREFERRED EMBODIMENTS

Figures 1, 2:
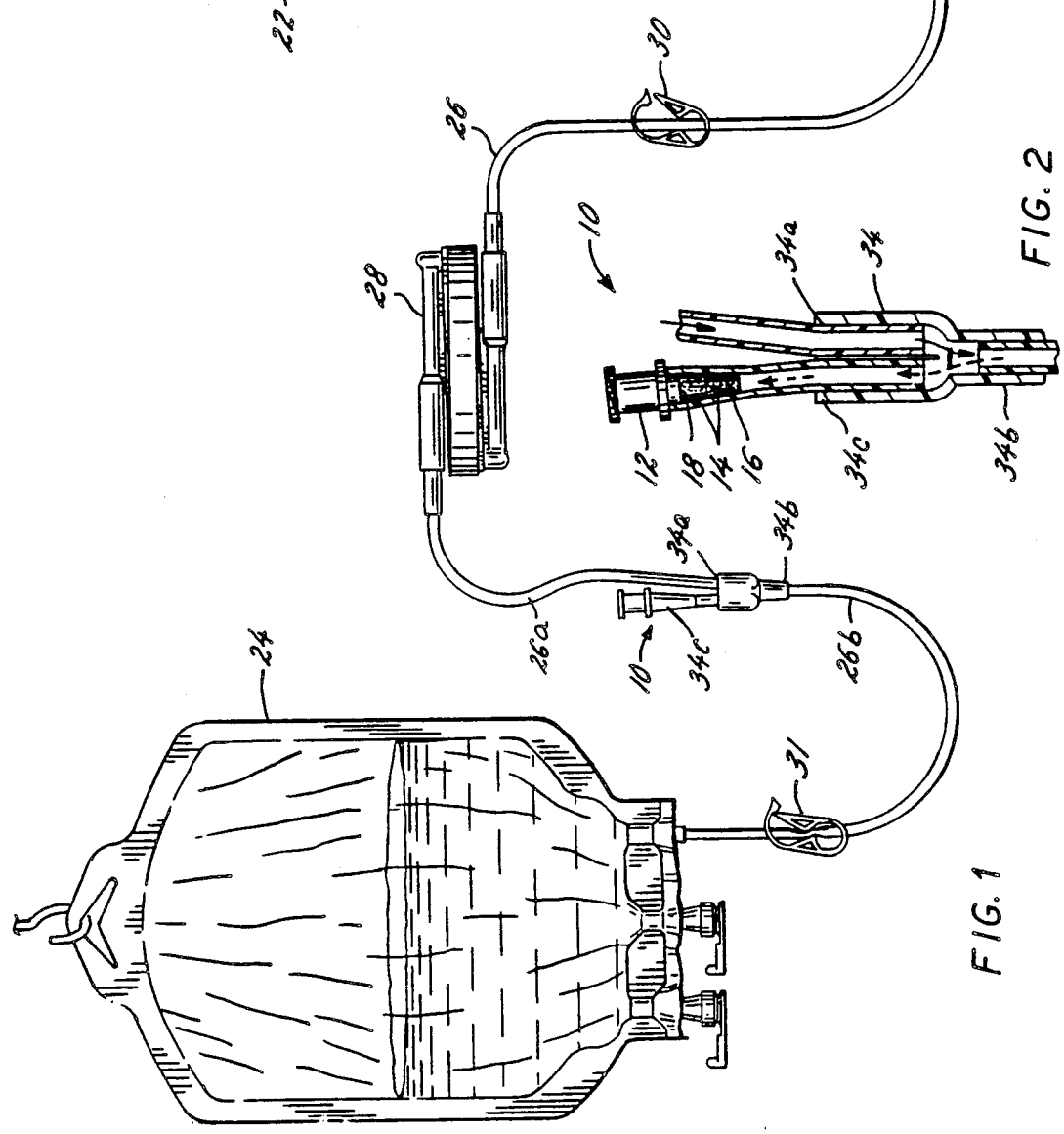
FIG. 1 is a perspective view of a fluid delivery system for the filtration of blood and blood components received from a donor and filtered prior to use, and including venting means.
FIG. 2 is a sectional view of venting means in accordance with the present invention taken along the line 2—2 of FIG. 1.

The venting means in accordance with the present invention is useful for venting gas from a liquid transfer or delivery system. Turning to FIG. 2, the venting means 10 of the present invention includes a housing 12 for holding a multilayer microporous membrane 14. The first microporous membrane layer 16 is liquid-wettable, that is, it is liquiphilic. By liquiphilic is meant that the microporous membrane layer is wetted by the liquid being processed in the transfer or delivery system. The second microporous membrane layer 18 is not wettable by the liquid being processed by the delivery system, that is, the second layer 18 is liquiphobic.

The liquiphilic layer 16 of the multilayer microporous membrane 14 is positioned in housing 12 to the inward side of venting means 10 so that liquiphilic layer 16 is in direct communication with a transfer line in which venting means 10 is to be carried. In this way liquiphilic layer 16 is the first layer to be contacted either by gas that is to be passed from the liquid transfer or delivery system or by the liquid being transferred or delivered by the system. The liquiphilic layer 16 is capable of passing gas therethrough so long as it remains unsaturated by the liquid being processed.

The liquiphobic layer 18 is capable of passing gas therethrough. Liquiphobic layer 18 is superimposed on liquiphilic layer 16 and is thus positioned on the outward side of venting means 10. The liquiphobic layer is thus not contacted by either gas or liquid in the delivery system until the gas or liquid has passed through the liquiphilic layer. Because of the liquid-wettable character of the liquiphilic layer 16 and the non-wettable character of liquiphobic layer 18, gas that contacts vent means 10 passes through vent means 10 so long as liquiphilic layer 16 remains unwetted by liquid. Once liquiphilic layer 16 becomes wetted with liquid, gas is no longer able to pass through the liquiphilic layer so venting means 10 becomes sealed. Accordingly, after the liquiphilic layer 16 is wetted by the liquid being processed, gas from outside the delivery system is foreclosed from entering the system through venting means 10. This is particularly advantageous when venting means 10 is used in a closed sterile system, for once any gases present in the system are vented, unwanted gases cannot reenter the closed system.

It will be appreciated that the liquiphilic and liquiphobic layers may be two separate layers, or they may be bonded together. In addition, the invention contemplates the use of a plurality of separate membrane elements combined together to form the liquiphilic microporous membrane and the use of a plurality of separate membrane elements combined together to form the liquiphobic microporous membrane. By the term plurality is meant two or more. The plurality of separate membrane layers may be individually prepared and bonded together by various means known to those skilled in the art. For example, the separate membrane layers may be bonded together by drying two or more layers maintained, in close contact. Alternatively, by way of illustration and not in limitation, the separate membrane layers may be prepared by passing the material used to form the membrane over a hot drum, against which it is held firmly by a tensioned felt web or other process sheet. In addition, it is likewise possible to combine a suitable supporting substrate with the membrane layer, if desired, and the supporting substrate may serve as a permanent support.

Because of the desirability of preventing distortion, and for greater strength and resistance to rupture, in most applications the housing of venting means 10 is preferably of a rigid construction, using rigid sheets or molded or cast plastic parts, or metal, thus making it possible for the device to resist fluid pressures up to the bubble point of the microporous membranes used. If high fluid pressures are not to be encountered, however, the housing can be of a flexible construction, in which case it can be made of flexible sheet material, such as polyvinyl chloride, vinyl chloride-vinylidene chloride copolymers, polyesters, polyethylene or polypropylene sheet. Moreover, it is also contemplated that for some applications the housing may be of the same material that the liquid transfer line is made of, such as the tubing used to make administration sets, for example. In those instances, the housing for the venting means is a portion of such tubing.

The housing may be constructed of rigid plastic material that is also transparent, such as polyethylene, polymethyl methacrylate, polymethyl acrylate, polymethyl pentene-1, polyvinyl chloride, and vinyl chloride-vinylidene chloride copolymers. Translucent materials, such as polypropylene, polyethylene, urea-formaldehyde, and melamine-formaldehyde polymers, can also be employed. Other plastic materials that are particularly suitable are polystyrene, polyamids, polytetrafluoroethylene, polyfluorotrichloroethylene, polycarbonates, polyester, phenol-formaldehyde resins, polyvinyl butyral, cellulose acetate, cellulose acetate propionate, ethyl cellulose and polyoxymethylene resins.

Metal housing can be used. Suitable metals include stainless alloys, such as nickel, chromium, vanadium, molybdenum, and manganese alloys. The housing material should, of course, be inert to the liquids being processed.

In accordance with the invention the liquiphobic microporous membrane must have sufficient liquiphobicity with respect to the liquid to be processed in the liquid delivery or transfer system that it will prevent the intrusion of the liquid being processed into the membrane. On the other hand the liquiphilic microporous membrane must have a pore size and sufficient liquiphilicity with respect to the liquid to be processed such that it will be wetted by the liquid sufficiently to prevent the passage of gas after it is wetted. It is preferred that both the liquiphilic and liquiphobic microporous membranes have, when combined for use in the venting means, an overall pore size such that the membranes form a bacterial barrier. When the pore size of the microporous membranes is so chosen the intrusion of bacteria into the system through the vent means is prevented. It will be readily appreciated that a vent means so configured is particularly well adapted for a closed system and/or for sterile liquid processing systems. Preferably, particularly in medical applications, the system is gamma-sterilizeable. Such vent means can even be used without a cap, if desired, although it is within the purview of the invention to cap the vent means if desired.

The microporous membranes suitable for use in the apparatus and method of the prevent invention may be made from any material capable of forming the membrane. Examples of suitable materials include polymeric materials such as polyamides, for example, nylon, such as Nylon 66, polyvinylidene difluoride and polytetrafluoroethylene. It will be appreciated that if the material chosen is normally liquiphobic, and it is desired to use this material for the liquiphilic microporous membrane, then the normally liquiphobic material will have to be treated so as to make it liquiphilic. The nature of the material used to make the membranes, the compatibility of the materials chosen for the membranes with one another and with the liquid to be processed all are factors to be considered in selecting a particular material for a membrane for a given end application. However, quite apart from those considerations, it is generally desirable and preferable that the same material be used for both the liquiphilic microporous membrane and for the liquiphobic microporous membrane so as to facilitate the bonding of the two different membranes to one another, if desired, as is preferred.

The preferred material for both the liquiphilic microporous membrane and the liquiphobic microporous membrane is polyvinylidene difluoride. Since polyvinylidene difluoride is hydrophobic, when the liquid to be processed is aqueous based, such as blood or blood components, the polyvinylidene difluoride used to make the microporous membrane must be treated so as to render it hydrophilic. Various treatments of the normally hydrophobic polyvinylidene difluoride to render it hydrophilic are known. However, the preferred method for making the polyvinylidene difluoride material hydrophilic is to treat a hydrophobic polyvinylidene difluoride microporous membrane, by subjecting it to gamma radiation in the presence of a hydrophilic agent, such as, for example, hydroxyethylmethacrylate (HEA). Preferably liquiphilic and liquiphobic polyvinylidene microporous membranes are secured to each other by placing them in intimate contact and drying them on a drum dryer.

The rate of air flow through the multilayer microporous membrane of vent means 10 can be tailored to the specific liquid transfer or delivery system of interest. The rate of air flow varies directly with the area of the membrane. Generally, the area of the membrane is designed to enable the liquid transfer or delivery system to be primed in a required time under the conditions of use. For example in medical applications it is desirable to be able to prime an intravenous set in from about 30 to about 60 seconds. In such applications as well as in other medical applications, the multilayer membrane may be in the form of a disc which has a diameter from about 3 mm to about 3 inches.

The pore size of the liquiphilic and liquiphobic microporous membranes is dependent on the liquid transfer or delivery system in which it is used, and, more particularly, whether the system is for medical or non-medical use. By way of illustration, where the vent means is to be incorporated in a system to be used for a medical application, the pore size of the liquiphilic and liquiphobic membranes is preferably selected so that at least one of the membranes provides a bacterial barrier to preclude entry of bacteria into the system. The pore size of the liquiphilic and liquiphobic microporous membranes may be the same or different. Generally the pore size of the hydrophobic membrane is in the range of from about 0.02 to about 3 micrometers and the pore size of the hydrophilic membrane is from about 0.04 to about 3 micrometers. Preferably the pore size of each of the membranes is in the range of from about 0.5 to about 0.8 micrometer and most preferably about 0.65 micrometer.

It will be appreciated that the force required to vent gas from the liquid transfer or delivery system through the venting means of the present invention varies inversely with the pore size of the membrane. Accordingly, the choice of pore size may be determined by the application in which the vent is used. For example, since the force required to pass gas through the vent means increases as the pore size of the membrane decreases, it may be desirable to choose a larger pore size (consistent with the other objectives of, for example, providing a bacterial barrier) where the delivery system is to be operated by hand so that the force required to use the system does not become too great for convenient hand use.

Turning to FIG. 1, there is shown a filtration system 20 for the filtration of blood or blood components. The filtration system includes a collapsible reservoir 22 which holds the blood or blood components to be filtered, a container 24 for receiving the filtered blood or filtered blood components, and a transfer line 26 in communication with both the reservoir 22 and receiving container 24. Filter means 28 is included in the transfer line 24 between the reservoir 22 and the receiving container 24. Filter means 28 is capable of removing harmful components, including, for example, leukocytes and the like, from the blood or blood components as blood or blood components pass through filter means 28. The preferred filter means in the case of packed red blood cells is the filter described in copending U.S. patent application Ser. No. 07/259,773, filed Oct. 19, 1988. The preferred filter means in the case of platelets is the filter described in U.S. Pat. No. 4,880,548. Of course, other filter means may be used in the delivery system without departing from the invention.

Vent means 10, as described above, is carried in transfer line 26 downstream of filter means 28 and upstream of receiving container 24. Transfer line 26 may also include clamps 30, 31 for closing off the transfer line to access from either reservoir 22 or receiving container 24.

As illustrated in FIG. 1, vent means 10 is preferably included in the transfer line 26 in the third leg 34c of a Y-connector 34. As illustrated, the first leg 34a of Y-connector 34 accommodates transfer line 26a which is in communication with filter means 28, while a second leg 34b of Y-connector 34 accommodates transfer line 26b in communication with receiving container 24. Clamp 31 is normally closed in order to allow gas in transfer line 26, 26a, 26b, filter means 28 and vent means 10 to be vented, and to prevent gas in the system from entering receiving container 24. After the entire transfer line has been primed, clamp 31 is opened to allow delivery of liquid into container 24.

In operation, reservoir 22 is squeezed to collapse it and thereby force a column of blood or blood components into transfer line 26. Clamp 30 has, of course, been opened to permit the flow of liquid into and through transfer line 26. Squeezing of reservoir 22 is continued to drive the column of blood or blood components through transfer line 26, through filter means 28 through transfer line 26a and into the first leg 34a of Y-connector 34. As the liquid from reservoir 22 advances, it pushes gas in the transfer line ahead of it until the gas reaches Y-connector 34. At Y-connector 34 gas ahead of the liquid column moves into the third leg 34c of Y-connector 34 and is vented from the transfer or delivery system through vent means 10. As the liquid in transfer line 26 continues its travel through the second leg 34b of Y-connector 34 and into transfer line 26b leading from Y-connector 34 to receiving container 24, gas in transfer line 26b is displaced toward and into the third leg 34c of Y-connector 34 where it passes out of the transfer or delivery system through vent means 10. As gas in transfer line 26b is displaced by advancing liquid, the liquid being transferred fills transfer line 26b with liquid. After transfer line 26b is filled with liquid, third leg 34c of Y-connector 34 also fills with liquid. The liquid then contacts and wets the first layer 16 of vent means 10. Wetting of first layer 16 by the liquid seals vent means 10 to passage of gas and thus forecloses gas from outside the system from entering into the system through vent means 10. After the system is primed, clamp 31 is opened to allow receiving container 24 to fill with filtered blood or filtered blood components.

Figure 3:
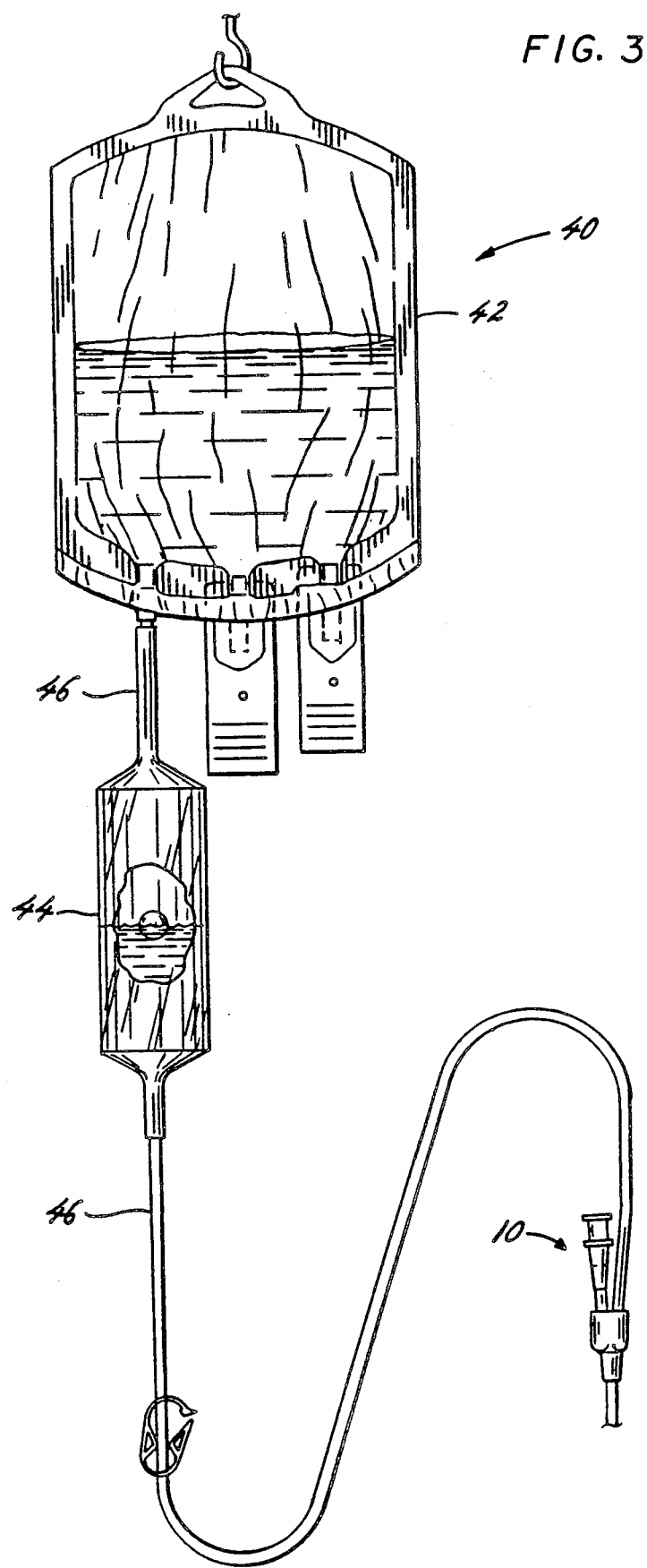
FIG. 3 is a perspective view of an intravenous feeding system, including venting means for the passage of gas from the administration set during priming.

It will be appreciated that venting means 10 can also be used to prime a liquid transfer or delivery system which is used for the percutaneous injection of liquids into a patient. Such systems, including for example an intravenous injection system as illustrated in FIG. 3 at 40 comprise a collapsible reservoir 42 which contains the liquid to be transferred or delivered, a drip chamber 44 for regulating the flow of liquid injected into the patient, and a transfer line 46 in communication with the reservoir 42 and drip chamber 44 and leading from drip chamber 44 to the injection needle or the like (not shown). In accordance with this embodiment of the present invention, venting means 10 as described above is carried in transfer line 46 downstream of drip chamber 44 but upstream of the terminal end of transfer line 46.

To prime the system, reservoir 42 is collapsed sufficiently to drive a column of liquid out of drip chamber 44. The moving column of liquid from drip chamber 44 drives a head of gas in the portion of transfer line 46 extending from drip chamber 44 toward the terminal end of transfer line 46. When the head of gas reaches vent means 10, it is passed out of transfer line 46 in the same manner as it is in the liquid transfer device of FIG. 2, as described above.

It will be appreciated that while the invention has been described in connection with the preferred embodiments and alternative embodiments are also possible. Thus, vent means 10 may be used in any liquid transfer or delivery system wherein it is desirable to purge the system of gas and prevent the ingress of gas into the system during the liquid transfer operation.

I claim as my invention:

1. A filtration system for the filtration of blood or blood components comprising:
 a collapsible reservoir which contains the blood or blood components to be filtered;
 a receiving container for receiving filtered blood or blood components;
 a transfer line in communication with said collapsible reservoir and with said receiving container;
 a filter capable of filtering said blood or said blood components carried in said transfer line between said reservoir and said receiving container; and
 venting means in said transfer line downstream of said filter and upstream of said receiving container, said venting means comprising:
 (a) a housing;
 (b) a first microporous membrane positioned in said housing to the inward side of said venting means in communication with said transfer line, said first microporous membrane being liquid-wettable by the liquid to be transferred in said filtration system; and
 (c) a second microporous membrane to the outward side of said venting means, said second microporous membrane capable of permitting gas to pass therethrough, said membranes arranged to permit gas to be vented from said venting means while said first microporous membrane remains unwetted with liquid, and to permit said venting means to be sealed when said first microporous membrane is wetted with liquid.

2. The system of claim 1 wherein said first microporous membrane and said second microporous membrane comprise a polymeric material selected from the group consisting of a polyamide, polyvinylidene difluoride and polytetrafluoroethylene.

3. The system of claim 2 wherein said first microporous membrane and said second microporous membrane comprise a polyamide.

4. The system of claim 3 wherein said polyamide is Nylon 66.

5. The system of claim 4 wherein the pore size of said first and said second microporous membrane is in the range of from about 0.2 to about 1.0 micron.

6. The system of claim 2 wherein said first microporous membrane and said second microporous membrane comprise polyvinylidene difluoride.

7. The system of claim 6 wherein the pore size of said first and said second microporous membrane is in the range of from about 0.2 to about 1.0 micron.

8. A method for priming a liquid transfer system wherein said system comprises a collapsible reservoir which contains a liquid and a liquid transfer line in communication with said collapsible reservoir, said method comprising:
 collapsing the collapsible reservoir to discharge liquid from said reservoir to said liquid transfer line; and
 maintaining sufficient pressure on said collapsible reservoir to cause the liquid to flow through said line toward the terminal end of the line causing any gas in the line to contact venting means in said liquid transfer line and allowing gas to pass from said line, said venting means comprising a first microporous membrane wettable by the liquid and a second microporous membrane capable of passing said gas, said first and second membranes positioned relative to each other so that gas or liquid first contacts said first membrane, said first microporous membrane permitting the passage of gas until it is wetted by said liquid, whereupon it is no longer capable of passing gas therethrough.

9. The method of claim 8 wherein said liquid transfer or delivery system comprises a percutaneous injection system for intravenous feeding, and includes a collapsible reservoir which contains the liquid to be injected into a patient, a drip chamber, a liquid delivery line having a first portion in communication with said collapsible reservoir and said drip chamber and having a second portion extending from said drip chamber to allow delivery of said liquid to said patient, said venting means carried in said second portion of said transfer line to permit said percutaneous injection system to be primed to remove gas from said system prior to injection of liquid into said patient.

10. The method of claim 9 wherein said first membrane and said second membrane comprise polyvinylidene difluoride and the pore size of each said membrane is from about 0.2 to about 1.0 micron.

11. A closed system for the transfer of a liquid comprising:
 a collapsible reservoir which contains the liquid to be transferred;
 a receiving container for receiving the liquid to be transferred;
 a transfer line in communication with said collapsible reservoir and with said receiving container; and
 venting means in said transfer line downstream of said collapsible reservoir and upstream of said receiving container, said venting means comprising:
 (a) a housing;
 (b) a first microporous membrane positioned in said housing to the inward side of said venting means in communication with said transfer line, said first microporous membrane being wettable by the liquid to be transferred; and (c) a second microporous membrane to the outward side of said venting means, said second microporous membrane capable of permitting gas to pass therethrough, said membranes arranged to permit gas to be vented from said venting means while said first microporous membrane remains unwetted with liquid, and to permit said venting means to be sealed when said first microporous membrane is wetted with liquid.

12. The system of claim 11 wherein said first microporous membrane and said second microporous membrane comprise a polymeric material selected from the group consisting of a polyamide, polyvinylidene difluoride and polytetrafluoroethylene.

13. The system of claim 12 wherein said first microporous membrane and said second microporous membrane comprise a polyamide.

14. The system of claim 13 wherein said polyamide is Nylon 66.

15. The system of claim 14 wherein the pore size of said first and said second microporous membrane is in the range of from about 0.2 to about 1.0 micron.

16. The system of claim 12 wherein said first microporous membrane and said second microporous membrane comprise polyvinylidene difluoride.

17. The system of claim 16 wherein the pore size of said first and said second microporous membrane is in the range of from about 0.2 to about 1.0 micron.

18. A method of preserving the sterility of a closed liquid transfer system wherein said system has a sterile internal environment, and said system comprises a collapsible reservoir which contains a liquid, and a liquid transfer line in communication with said collapsible reservoir, said method comprising:

collapsing the collapsible reservoir to discharge liquid from said reservoir to said liquid transfer line; and maintaining sufficient pressure on said collapsible reservoir to cause the liquid to flow through said line toward the terminal end of the line causing any gas in the line to contact venting means in said liquid transfer line and allowing gas to pass from said line, said venting means comprising a first microporous membrane wettable by the liquid and a second microporous membrane capable of passing said gas, said first and second membranes positioned relative to each other so that gas or liquid first contacts said first membrane, said first microporous membrane permitting the passage of gas until it is wetted by said liquid, whereupon it is no longer capable of passing gas therethrough.

19. The method of claim 18 wherein said first membrane and said second membrane comprise polyvinylidene difluoride and have a pore size of from about 0.2 to about 1.0 micron.

* * * * *